United States Patent
Emmrich et al.

(10) Patent No.: US 6,582,714 B1
(45) Date of Patent: Jun. 24, 2003

(54) ARTICLE FOR INSERT CONTROL BY PASSIVE EVAPORATION OF AN ACTIVE INGREDIENT

(75) Inventors: Robert R. Emmrich, Racine, WI (US); John W. Mikkonen, Village of Pleasant Prairie, WI (US); Thomas A. Lajiness, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 08/419,219

(22) Filed: Apr. 10, 1995

(51) Int. Cl.$^7$ .................. A01N 53/00; A01N 25/10; A01N 25/34

(52) U.S. Cl. .................. 424/409; 424/405; 424/411; 424/413; 424/416; 514/531

(58) Field of Search ................ 424/405, 402, 424/403, 409, 411, 413, 416; 428/248; 514/65, 919

(56) References Cited

U.S. PATENT DOCUMENTS

| | | | |
|---|---|---|---|
| 339,810 A | 4/1886 | Regan | 424/405 |
| 2,720,013 A | 10/1955 | Clarke | 424/405 |
| 2,956,073 A | 10/1960 | Whetstone et al. | 260/461 |
| 3,044,885 A | 7/1962 | Loehr | 424/405 |
| 3,116,201 A | 12/1963 | Whetstone et al. | 167/22 |
| 3,295,246 A * | 1/1967 | Landsman et al. | 43/131 |
| 3,318,769 A | 5/1967 | Folckemer et al. | 167/42 |
| 3,620,453 A | 11/1971 | Gancberg et al. | 239/60 |
| 4,103,450 A | 8/1978 | Whitcomb | 43/131 |
| 4,178,384 A | 12/1979 | Ensing | 424/405 |
| 4,439,415 A | 3/1984 | Hennart et al. | 424/405 |
| 4,631,231 A | 12/1986 | Stendel et al. | 424/405 |
| 4,765,982 A | 8/1988 | Ronning et al. | 424/405 |
| 4,796,381 A | 1/1989 | Kauth et al. | 424/405 |
| 4,860,488 A | 8/1989 | Shigetoyo | 43/129 |
| 4,879,117 A | 11/1989 | Rombi | 424/405 |
| 4,900,876 A * | 2/1990 | Bushman et al. | 119/106 |
| 4,901,674 A * | 2/1990 | Bushman et al. | 119/106 |
| 4,940,729 A | 7/1990 | Matthewson | 514/521 |
| 4,966,796 A | 10/1990 | Aki et al. | 424/445 |
| 5,091,183 A | 2/1992 | Yano et al. | 424/405 |
| 5,156,843 A | 10/1992 | Leong et al. | 424/411 |
| 5,198,287 A | 3/1993 | Samson et al. | 428/248 |
| 5,229,122 A | 7/1993 | Chadwick et al. | 424/408 |
| 5,252,387 A | 10/1993 | Samson et al. | 428/248 |
| 5,290,770 A | 3/1994 | Matthewson | 514/86 |

FOREIGN PATENT DOCUMENTS

| | | |
|---|---|---|
| DE | B12 30 259 | 1/1962 |
| DE | 3938664 A1 | 5/1990 |
| DE | 0 477 676 A1 | 4/1992 |
| EP | 253 640 A3 | 1/1988 |
| EP | 0 596 317 A1 | 5/1994 |
| GB | 1236343 | 6/1971 |
| GB | 2 151 926 A | 7/1985 |
| GB | 2 276 320 A | 9/1994 |
| JP | 96/04786 | 2/1994 |
| WO | WO 96/04786 | 2/1996 |
| ZA | 711214 | 2/1971 |

OTHER PUBLICATIONS

Mori et al., Chemical Abstracts, vol. 121, 24 8663.*
Pflanzenschutz Nachrichten Bayer, E.D. Mrusek et al, Bayer AG, 1995, pp. 1–48, Jul. 1995.*
Patent Abstracts of Japan, vol. 13, No. 556 (C–664). Abstract for JP,A,01 230 502 (Fumakilla).
Chemical Abstracts, vol. 117, No. 1, abstract No. 2831. Abstract for Peop. Rep. of China patent, Cui, CN 1056911A.
Database WPI, Section CH.,Week 9013, Derwent Publications Ltd., London, GB; AN 90–096004. Derwent abstract for JP,A,02 048 507 (Sumitomo Chem. Ind. KK).
Pflanzenschutz Nachrichten Bayer (Special Edition) Published by Bayer AG, Copyright 1995 by Bayer AG, Leverkusen.
Chemical Abstracts, vol. 100, No. 21, abstract No. 169902. Abstract of Masachika et al.
Patent Abstracts of Japan, vol. 12, No. 344. Abstract for Fumitoshi, JP,A,63 101 301 (Fumakilla).
Database WPI, Section CH.,Week 8136, Derwent Publications Ltd., London, GB; AN 81–65092D. Derwent abstract for JP,A,56 090 004 (Earth Seiyaku KK).

* cited by examiner

Primary Examiner—Neil S. Levy

(57) ABSTRACT

An insect control article to control flying insects. The insect control article has a substrate that is impregnated with an active insect control ingredient that is available for passive evaporation. The active insect control ingredient is selected from the group consisting of transfluthrin, prallethrin, tefluthrin, esbiothrin, and combinations thereof. The method of the invention for controlling flying insects includes providing an insect control article having a substrate that is impregnated with an active insect control ingredient available for passive evaporation, wherein the active insect control ingredient is selected from the group consisting of transfluthrin, prallethrin, vaporthrin, teflurthrin, esbiothrin, DDVP, and combinations thereof. The insect control article is then placed in an environment with air movement in such a manner that the substrate of the insect control article is exposed to the air movement, and the active insect control ingredient impregnated within the substrate is allowed to evaporate passively into the air.

5 Claims, No Drawings

ARTICLE FOR INSERT CONTROL BY PASSIVE EVAPORATION OF AN ACTIVE INGREDIENT

TECHNICAL FIELD

The present invention relates generally to insect control and more particularly to insect control articles that are effective in killing or repelling mosquitoes within the air of a room or the volume of air in the vicinity of a person sitting on a patio, at a picnic table, or the like.

BACKGROUND ART

For certain applications, it is important to be able to control flying insects for six to ten hour or even longer periods within defined spaces such as the enclosed space of a bedroom. That duration of insect control is desirable, for example, to protect a sleeper occupying an unscreened room from mosquitoes for a single night. It is also useful to be able to deliver an insect controlling amount of active ingredient nightly for multiple nights in succession. Successful flying insect control is also useful in other living spaces, including even screened areas that for any reason are still subject to invasion by flying insects, as well as outdoor areas such as a patio, a picnic table, or the like.

Traditionally, articles or devices that dispense insecticide vapors to control such insects in such settings require heating or burning a liquid or solid substrate to evaporate the active ingredients. For example, conventional citronella candles have long been used for such purposes. Burning insect coils are also commonly used to achieve a night's insect control or to control mosquitoes or other insects for an outdoor party or picnic. The product sold by S. C. Johnson & Son, Inc. of Racine, Wis. under the mark "45 Nights®" is an example of a type of product known in the art for delivering insect control over repeated periods of use, such as a nightly use in an unscreened bedroom. The 45 Nights® product is an example of conventional heated, liquid evaporation insect control products.

The products referred to above all can be effective, within certain limits. However, products that require a heat source also require a safe burning site, in the case of insect coils, for example, and a safe location and source of house electrical current for typical heated evaporation products. Products exist that are designed to avoid some of these difficulties by employing passive evaporation of insect control active ingredients without the application of heat. However, they have problems and limitations of usefulness when compared to products and insect control strategies employing the application of heat.

For example, Regan, U.S. Pat. No. 339,810 uses a tobacco preparation as a repellent that is first soaked into cloth or paper and then dried. The repellent active ingredient is reported to evaporate from the substrate to repel insects. More recent technology has included the use of pyrethrum or pyrethroid materials as passively evaporated insect control active ingredients. For example, see Landsman, U.S. Pat. No. 3,295,246. Ensing, U.S. Pat. No. 4,178,384 employs pyrethroids as repellents applied to the locus to be protected.

Whitcomb, U.S. Pat. No. 4,130,450 describes an insecticide-impregnated, open, low-density web that provides an expanded surface that may be loaded with contact insecticides, including pyrethrum and synthetically prepared insecticides. Whitcomb prefers the use of micro-encapsulated pyrethrum to avoid pyrethrum instability when exposed to ultraviolet light and oxygen. Whitcomb mentions that the web may be hung to permit vaporization of the active ingredient to combat flies. Similarly, Chadwick et al., U.S. Pat. No. 5,229,122 utilizes a mixture of micro-encapsulated and non-micro-encapsulated active ingredients, noting that any known pesticide may be used for the purpose. Pyrethrum or a pyrethroid equivalent are referred to as possible pesticides. The preparation is used to coat surfaces, although it is also noted that the vapor phase of the pesticides may be valuable.

Kauth et al., U.S. Pat. No. 4,796,381, is an example of the use of paper or textile strips impregnated with insecticide that is allowed to evaporate to control insect pests. The Kauth et al. materials utilize pyrethroids and, in particular, vaporthrin, permethrin, and bioallethrin. However, the devices of Kauth et al. are designed to be hung in closets or placed in drawers, suggesting that they are understood to be inadequate to protect larger, more open spaces. Nothing in Kauth et al. suggests any ability of their paper or textile strips to control insects in relatively large air volumes when held within a moving air stream.

Samson et al., U.S. Pat. Nos. 5,198,287 and 5,252,387 disclose a fabric for use in a tent, the fabric including a coating that contains evaporatable insecticides, and in particular, permethrin. Again, a confined space is being protected.

Aki et al., U.S. Pat. No. 4,966,796, utilizes a pyrethroid insecticide on kraft paper, with additional layers of untreated kraft paper added to create a material useful for making an insect-resistive packaging material or bag.

Landsman teaches the use of an insecticide-soaked and then dried paper that is coated with resin to slow evaporation of the active ingredient. The resin coating is deemed important to make an insecticide product that will be effective over a usefully long period of time. Example formulations cited in Landsman include pyrethrins as active ingredients. The Landsman product is not intended to protect large volumes of air and is also an example of the difficulty known in the art of achieving protection over an extended period of time because of the evaporative rate of active ingredients.

Ronning et al., U.S. Pat. No. 4,765,982 is an example of the use of micro-encapsulated active ingredients to achieve a sustained release insect control effect. Pyrethroids, either synthetic or "natural," are cited as useful. The Ronning et al. insecticidal device may be hung in the open to achieve a repellent effect in a restricted locale to drive insects from a nest or the like.

Yano et al., U.S. Pat. No. 5,091,183 and Matthewson, U.S. Pat. Nos. 4,940,729 and 5,290,774 cite specific insecticidal compounds for volatilization. Yano et al. specifically discusses the use of impregnated papers for heatless evaporation of an insecticidal compound.

Clarke, U.S. Pat. No. 2,720,013, describes the use of a fabric material into which active ingredients are pressed or fused. Pyrethrum is cited as useful not by itself but as at least one element in a mixture of insecticides. The Clarke fabric material is designed to be adhered to the blades of an electric fan so that the insecticide will be directed into the area ventilated by the fan.

In overview, although passive evaporation of insecticides, including pyrethroids, is known in the art, the nature of those materials has been such that the attention of the art generally has been directed to their application to closely restricted spaces or to the area in the immediate vicinity of the materials. Within that context, the art has focused on the need to provide for artificially extending the longevity of insect control by use of a slow release structure or regimen of some sort, or the like. Heat and not passive evaporation has been the predominant means to achieve practical distribution of insecticide throughout a large volume of air, and heated evaporation from a liquid reservoir has been the practical means of achieving protection over a multiplicity of days.

SUMMARY OF THE INVENTION

The insect control article of the invention to control flying insects is summarized in that a substrate is impregnated with an active insect control ingredient that is available for passive evaporation. The active insect control ingredient is selected from the group consisting of transfluthrin, prallethrin, 0tefluthrin, esbiothrin, and combinations thereof. Preferably, the active insect control ingredient includes at least one of transfluthrin and tefluthrin, and most preferably the active control ingredient includes at least transfluthrin.

The method of the invention for controlling flying insects is summarized in that it includes the initial step of providing an insect control article having a substrate that is impregnated with an active insect control ingredient available for passive evaporation, wherein the active insect control ingredient is selected from the group consisting of transfluthrin, prallethrin, vaporthrin, tefluthrin, esbiothrin, DDVP, and combinations thereof. Preferably, the active insect control ingredient includes at least one of transfluthrin and tefluthrin, and most preferably the active control ingredient includes at least transfluthrin. The insect control article is then placed in an environment with air movement in such a manner that the substrate of the insect control article is exposed to the air movement. The active insect control ingredient impregnated within the substrate then is allowed to evaporate passively into the air.

DETAILED DESCRIPTION OF THE INVENTION

As used in this specification, "insect control" of flying insects is defined as at least repelling and preferably rendering the flying insects moribund. "Passive evaporation" is the process by which an active insect control ingredient evaporates from a substrate into the atmosphere through molecular separation, without the application of thermal energy to the substrate, whether by burning the substrate, use of a heating element, or other means. "Molecular separation" shall be deemed achieved if particles of an active insect control ingredient cannot be detected by conventional light scattering counter techniques using an instrument such as the Climet Model CI-7300 Light Scattering Counter, made by Climet Instruments Company of Redlands, Calif. This instrument is capable of detecting airborne particles as small as 0.3 microns. "Effective amount" shall mean an amount sufficient to attain the desired purpose. A substrate shall be deemed to be "impregnated" with an active insect control ingredient if that ingredient is generally distributed within or on the material of the substrate in such a manner that the ingredient is directly held within or on the substrate and is supported thereby. An ingredient held within or borne by intervening carriers or delayed-release means such as microcapsules, particles primarily composed of materials other than the ingredient, plastic materials, or the like that are then distributed within a substrate shall not be considered to be "directly" held within or on the substrate. "Porous" and related terms shall be understood to describe not only materials literally having pores but also, without restriction, loose or open materials and other materials that are fibrous, reticulate, matted, or woven and through or into which fluids may pass.

The insect control article to control flying insects of the present invention falls within the class of insect control articles that include a substrate impregnated with an effective amount of an active insect control ingredient available for passive evaporation from the substrate. The substrate of the invention may be made of any material capable first of receiving and holding an active insect control ingredient and then of releasing it by passive evaporation. Suitable materials include, without limitation, paper-board, open pore cellulosic materials, coiled corrugated paper, woven cloth and non-woven pads or felts of any suitable fiber, gels, absorbent solid-porous foams such as a reticulated, open cell polyurethane foam, and finely divided, channeled, or honeycombed structures molded of non-porous plastics. Depending on the context within which the insect control article of the invention is to be used, either coiled corrugated paper or a piece of flat, open-surfaced paper presently is preferred, although the use of the molded plastic structures referred to has advantages of manufacturing convenience.

As is noted in the discussion of Background Art, above, the art teaches the use of various insecticides for passive evaporation for the control of insects, for the most part although not exclusively in drawers, closets, tents, and other very limited spaces or as insecticidal barriers intended to affect insects in close proximity to a treated carrier strip or the like. This teaching of the art would lead one to expect equally successful flying insect control from the passive evaporation of pyrethrum, sometimes microencapsulated (e.g. Landsman, Clarke, Whitcomb, Chadwick et al.), pyrethroids in general (e.g. generic references in Ensing, Ronning, et al., and elsewhere), and particular pyrethroids, such as permethrin (Samson et al., U.S. Pat. No. 5,189,287), vaporthrin, permethrin, bioresmethrin, bioallethrin, kadethrin, decis, cyfluthrin, and fenfluthrin (Kauth et al.) and permethrin, deltamethrin, cyhalothrin, and cypermethrin (Chadwick et al.). These examples are intended to be illustrative and not exhaustive.

To the limited extent that the art is suggestive or predictive of success, all of these insecticides would appear equally attractive, along with apparently equally attractive non-pyrethroid insecticides (Whitcomb, Clarke, etc.). However, in research discussed below, the present inventors have found that in fact, with the possible exception of vaporthrin and dichlovos (DDVP), the examples of these materials that were tested were not sufficiently effective to be employed successfully for the practical control of mosquitoes, for example, in a space as large as a typical sleeping room or in the open area surrounding a picnic table or patio.

"Practical control" shall be understood to require, at the minimum, the ability of a substantially planar substrate, such as a flat paper or cloth, not larger than about 645 cm$^2$ (100 in$^2$) to achieve at least 50% repellency of mosquitoes within a volume of air not less than 27 m$^3$ within 20 minutes when that substrate is impregnated with not more than a gram of insect control active ingredient and when the substrate is suspended directly in the airflow of a common 51 cm (20 inch) house fan, in accordance with the fan chamber test protocol, described below. This shall be referred to herein as the "minimum practical control standard."

Preferred is the level of practical control demonstrated by the ability of a standard high air-transmitting substrate, described below, impregnated with not more than 1 gram of insect control active ingredient to achieve that same repellency effect within 30 minutes when subjected to an airflow through the substrate of not more than 0.06 m³ per minute. The standard high air-transmitting substrate by which this level of practical control may be determined is a 0.5 cm thick, 4.5 cm diameter coil of common corrugated cardboard, with the channels of the corrugation presented endwardly to the direction of air flow. This shall be referred to herein as the "preferred practical control standard."

It has now been discovered that unexpected and favorable results are achieved in the practical control of flying insects when the active insect control ingredient used in the insect control article of the invention is selected from the group consisting of the pyrethroids transfluthrin, prallethrin, vaporthrin, tefluthrin, and esbiothrin, or the non-pyrethroid DDVP and combinations thereof. To most easily achieve the minimum practical control standard and especially when the preferred practical control standard is to be achieved, it is preferred that the active insect control ingredient include at least one of transfluthrin and tefluthrin. Of those two, transfluthrin is preferred as less irritating and otherwise objectionable for use in the presence of humans.

The particular active insect control ingredients disclosed now have been found to be sufficiently effective as insect control active ingredients that their airborne concentration is sufficient to achieve control of flying insects and, in particular, of mosquitoes and flies, when these ingredients are delivered by passive evaporation into the air when the substrate of the invention is placed in an environment with air movement at air temperatures between 10° C. and 45° C. At the same time, these selected materials' vapor pressures at those temperatures are low enough that it is practical and economical to use them as active ingredients on substrates of a convenient size in amounts sufficient to achieve such insect controlling concentrations over time periods long enough to be sufficient to protect a room overnight or even for a series of nights. A useful commercial goal is to achieve protection for at least thirty consecutive nights of use. By use of the active ingredients of the invention, this goal is within practical reach.

Any effective conventional method may be used to impregnate the substrate with the active insect control ingredient. Typically, the substrate is impregnated with the active insect control ingredient by dissolving an appropriate amount of the active insect control ingredient in a solvent, thoroughly wetting the substrate with the solvent, and then drying the substrate to evaporate the solvent contained in the substrate and leave the substrate impregnated with the active insect control ingredient. If air transmission through the substrate is desired, the substrate preferably is not coated or printed with a layer of the active insect control ingredient. This is because the coated or printed surface is likely to inhibit air movement through the substrate, thereby decreasing the rate of passive evaporation of the active insect control ingredient. However, coating or printing a substrate may be effective when air is to merely pass over and not through the substrate.

The amount of active insect control ingredient per square centimeter of substrate necessary to be effective to control flying insects in an insect control article of the invention will depend upon the overall size of the substrate used, the rate of air movement over or through the substrate, and the longevity of effectiveness desired. Preferably, the active insect control ingredient is present approximately in an amount of from 0.1 to 10 milligrams per square centimeter of macro surface area, when conventional, essentially planar substrates such as papers, corrugated cardboard coils, or felts are used. For the purpose of this discussion, "macro surface area" means the surface area as measured with a ruler or similar device, as opposed to the micro surface area as measured taking into account porosity, surface convolutions, finely divided materials, and the like. A very porous or finely divided substrate may hold additional amounts of active insect control ingredient in a given macro surface area, allowing for use of a smaller macro surface area of substrate. However, the preferred amounts of the active insect control ingredients identified above per square centimeter of macro surface area result in a substrate of a size convenient to handle and otherwise deal with when the material of the substrate is common paper, felted and woven materials, and the like, and when substantial insect control within a typical sleeping room, for example, is to be achieved for at least eight hours by placing the substrate in the air flow generated by conventional electric cooling fans. Disks of paper approximately 15 to 25 cm in diameter or approximately 25 cm square pieces of felted or woven cloth have proved convenient sizes for use with common, free-standing house fans, such as the square, 51 cm (20 inch) box fans conventionally available for household use. However, the invention is not limited to these precise sizes.

The insect control article of the present invention can be placed in any environment where there is air movement that will pass through or over the impregnated substrate, thereby allowing the active insect control ingredient to continuously passively evaporate into the atmosphere for an extended period of time. Suitable environments include enclosed rooms as well as volumes of open air space, such as patios, the area around a picnic table, and the like, with air movement provided by fans, air circulating systems, open windows, or the like.

In one embodiment of the present invention, the insect control article includes hanger means for suspending the impregnated substrate in a suitable environment provided with air movement to allow the active insect control ingredient to passively evaporate into the atmosphere. In another embodiment, the article includes attachment means for attaching the impregnated substrate to means for circulating air. Examples of such means for circulating air include but are not limited to conventional room fans. Examples of suitable hanger or attachment means for both embodiments include hooks, strings, mechanical clips and fasteners, adhesives, and the like. Any such means provided on the substrate should not substantially block the passage of air through or over the substrate.

When the impregnated substrate is attached to a fan, the impregnated substrate preferably is attached at a point separated from the fan blades sufficiently to allow the air stream to pass from the blades and then through or over the substrate, thereby facilitating the passive evaporation of the active insect control ingredient from the substrate. Attachment directly to the surface of the fan blades is not deemed satisfactory, because the air stream may not pass sufficiently through or over the substrate to achieve adequate insect control, an effect demonstrated in the Examples, below.

The method of the invention for controlling flying insects includes, as a first step, providing an insect control article to control flying insects that includes a substrate that is impregnated with an active insect control ingredient selected from the group consisting of transfluthrin, prallethrin, vaporthrin, tefluthrin, esbiothrin, DDVP, and combinations thereof. The insect control article is then placed in an environment with air movement, and the substrate of the insect control article is exposed to the moving air. Preferably, the substrate is located at a selected distance from any fan or equivalent means for moving air that is being used to create air movement. The active insect control ingredient with which the substrate is impregnated is then allowed to passively evaporate into the air.

The following non-limiting examples demonstrate the insect control article and method of the invention. The invention should not be understood as being limited to these particular examples, which are only illustrative.

EXAMPLE 1

Olfactometer Tests

The olfactometer test provides a means for measuring the effect of a volatile active ingredient on flying insects under precisely controlled conditions. Mosquitoes are used as the test insect. In this and the other Examples, below, the mosquitoes were *A. aegypti*. The olfactometer used for the olfactory tests described below generates two uniform, laminar flow air streams. These air streams consist of a target air stream superimposed upon and centered within a carrier air stream.

The olfactometer provides a square testing surface with an area of 929 cm$^2$. The testing area consists of a circular target area of 42 cm$^2$ centered on a square background surface area of 887 cm$^2$. In the tests described, a 200 ml/min flow of carbon dioxide was introduced into the carrier air stream to activate the mosquitoes. The carrier air stream contained 65% to 70% relative humidity and had a temperature of about 25° C. The flow rate of the carrier air stream was 300 to 350 liters/min. The target air stream contained 72% to 78% relative humidity and had a temperature of 33° to 35° C. Elevated temperature and humidity at the level described for the target air stream are known to be attractive to mosquitoes. The flow rate of the target air stream was 12 liters/min.

The olfactometer has an air flow duct through which the carrier air flow strewn passes. A glass cylinder having one closed and one open end, an internal diameter of 6 cm and a depth of 14 cm is located within the air flow duct, with the longitudinal axis of the glass cylinder oriented parallel to the direction of flow of the carrier air flow stream, with the open end of the cylinder pointing down stream. The target air stream is generated by releasing a flow of temperature and humidity conditioned air into the glass cylinder near its closed end, from which point the air flows the length of the glass cylinder to exit at its open end.

Active insect control ingredients to be tested are impregnated in a filter paper test substrate (Grade 615 from VWR Scientific Inc.) having a length of 28 cm and a width of 10 cm. The filter paper test substrate is folded into a fluted cylinder and inserted coaxially within the glass cylinder to rest at a location between the point where the air is released into the glass cylinder and the open end of the glass cylinder. By this arrangement, the target air stream is caused to pass over the surface of the filter paper test substrate so that any active insect control ingredient present in the filter paper test substrate may evaporate into the target air stream before the target air stream exits the glass cylinder to continue, embedded within the flow of the carrier air stream.

Cubic test cages having 30.5 cm edges were constructed of four glass panels, with two opposing sides of the cubic test cages being open. One open side was designated the test panel and was covered with an airflow-transmitting, mosquito-retaining mesh. The opposite open side was covered with a closeable sleeve made of a tubular, open-weave, mosquito-retaining fabric well known in the art as "stockinet." For any given test, the test cage normally contained from 250 to 350 female mosquitoes.

The test cage was placed in the air stream with the test panel facing and perpendicular to the direction of flow of the air streams of the olfactometer. In order to allow the mosquitoes to become activated by the carbon dioxide of the air streams, the test cage first was placed in the olfactometer for an initial 5 minute conditioning exposure. The test cage then was removed from the olfactometer for 3 minutes and then placed back in the olfactometer for a second 5 minute conditioning exposure. The test cage was again removed from the olfactometer for 3 minutes, during which time a control filter paper test substrate was inserted within the glass cylinder of the olfactometer. The test cage was then placed on the olfactometer for a 10 minute control exposure. The same procedure was repeated, using each time a filter paper test substrate impregnated with increasing amounts of active insect control ingredient.

All mosquito activity was recorded on video tape, and mosquitoes were observed to be either attracted to or repelled from the target area to varying degrees. Following the first three minutes of each exposure, populations of mosquitoes present on the target area were counted at 15 second intervals. Population means were then calculated, and these means were used to calculate response levels. Dose levels corresponding to response levels at which 90% of the control population was driven from the target by the active insect control ingredient ($RD_{90}$) were calculated using the dose-response data. To facilitate comparison, a weight index was calculated for each substance tested. The weight index is defined as the ratio of the weight of the active insect control ingredient versus the weight of DEET (N,N-diethyl-meta-toluamide) that is necessary for each material to achieve a repellent dose of 90% when applied to a selected amount of substrate in a moving air stream at a standard air temperature of 25° C.

The $RD_{90}$ data in milligrams/filter paper test substrate and the resultant weight indices for the active insect control ingredients are as follows, listed in order of increasing weight index:

| ACTIVE INSECT CONTROL INGREDIENT | mg to reach $RD_{90}$ | WEIGHT INDEX |
|---|---|---|
| Transfluthrin | 0.57 | 0.0059 |
| Tefluthrin | 1.3 | 0.014 |
| Esbiothrin | 4.5 | 0.047 |
| Vaporthrin | 5.3 | 0.058 |
| Bioallethrin | 5.5 | 0.058 |
| Prallethrin | 5.5 | 0.058 |
| Pentecyclothrin (Zhong X1) | 8.1 | 0.085 |
| Allethrin (90% active) | 8.0 | 0.085 |
| Pyrethrum Extract (51% active) | 30 | 0.32 |
| DDVP | 40 | 0.42 |
| DEET | 95 | 1.00 |
| Propoxur (Baygon) | >120 | >1.26 |
| Citronella | 475 | 5.0 |
| Cyphenothrin | ~1000 | ~10.5 |
| Permethrin | >1000 | >10.5 |
| Cyfluthrin | >1000 | >10.5 |

Differences in effective repellency per gram of active ingredient can be observed in the data provided, above, that vary by many orders of magnitude. Olfactometer tests of active insect control ingredients can be conducted at less expense and more quickly than other tests and therefore provide a useful first screening technique. Nevertheless, the conditions of olfactometer tests are not the same as use conditions for practical flying insect control. Thus, while from the results, above, transfluthrin, tefluthrin, vaporthrin, bioallethrin, prallethrin, and pentecyclothrin all would appear to be comparable candidates for use in practical flying insect control, tests that better mimic actual use show that not to be the case, emphasizing the fact that the usefulness of any given active ingredient cannot be predicted from past uses under similar but nevertheless distinct conditions.

EXAMPLE 2
Volatility and Activity Index Calculations

The "volatility index" of insect control active ingredients is a measurement of their concentration in the air relative to DEET at 20 to 25° C. If vapor pressure is known, concentration in the air in grains/liter may be estimated by use of the following equation, which is derived from the ideal gas equation:

$$C = \frac{M[P_2(T_1/T_2)/760]}{22.4}$$

wherein C is the concentration in air of the active insect control ingredient in grams per liter at the temperature of interest $T_2$, M is the molecular weight of the active insect control ingredient, $P_2$ is the vapor pressure of the active insect control ingredient in torr at $T_2$, and $T_1$ is 273° K. $T_2$ is expressed in degrees Kelvin.

With respect to the following active insect control ingredients, the calculated concentrations in air and the resultant volatility indices are as follows:

| ACTIVE INSECT CONTROL INGREDIENT | CONCENTRATION IN AIR | VOLATILITY INDEX |
| --- | --- | --- |
| Cyfluthrin | <7.11 × 10$^{-9}$ | <0.00041 |
| Permethrin | 7.11 × 10$^{-9}$ | 0.00041 |
| Cyphenothrin | 1.85 × 10$^{-8}$ | 0.0011 |
| Transfluthrin | 6.09 × 10$^{-8}$ | 0.0035 |
| Pentecychlothrin (Zhong X1) | 3.64 × 10$^{-7}$ | 0.021 |
| Prallethrin | 5.80 × 10$^{-7}$ | 0.034 |
| Pyrethrum Extract (51% active) | <0.8 × 10$^{-7}$ | <0.047 |
| Bioallethrin | 1.46 × 10$^{-6}$ | 0.085 |
| Allethrin | 1.92 × 10$^{-6}$ | 0.112 |
| Esbiothrin | 5.35 × 10$^{-6}$ | 0.311 |
| Vaporthrin | 9.75 × 10$^{-6}$ | 0.567 |
| Tefluthrin | 1.37 × 10$^{-5}$ | 0.797 |
| DEET | 1.72 × 10$^{-5}$ | 1.00 |
| DDVP | 2.63 × 10$^{-5}$ | 1.53 |
| Citronella | ~9.7 × 10$^{-4}$ | ~56.0 |

The "activity index" is obtained by the multiplying the volatility index and the weight index. The activity index is an attempt to predict the combined effect of volatility and potency by weight in the usefulness of an insect control active ingredient for insect control of flying insects by passive evaporation. The following activity indices were calculated from the volatility and weight indices given, above:

| ACTIVE INSECT CONTROL INGREDIENT | ACTIVITY INDEX |
| --- | --- |
| Transfluthrin | 0.00002 |
| Pentecychlothrin | 0.0018 |
| Prallethrin | 0.0020 |
| Bioallethrin | 0.0049 |
| Permethrin | >0.004 |
| Allethrin (90% active) | 0.0095 |
| Pyrethrum Extract (51% active) | <0.015 |
| Tefluthrin | 0.011 |
| Cyphenothrin | ~0.011 |

-continued

| ACTIVE INSECT CONTROL INGREDIENT | ACTIVITY INDEX |
| --- | --- |
| Esbiothrin | 0.0146 |
| Vaporthrin | 0.033 |
| DDVP | 0.60 |
| DEET | 1.00 |
| Citronella | ~280 |

While the activity index provides a logical prescreening technique for ruling out ingredients likely to not merit further testing, the relative success of the remaining ingredients in subsequent tests that model actual use is not perfectly predictable by comparing their activity index numbers. This lack of correlation between one sort of testing situation or use and another demonstrates why statements in the art about the general usefulness of whole classes of active ingredients, and even the use of particular ingredients in other applications, in fact do not enable one skilled in the art to achieve practical flying insect control without further discovery.

EXAMPLE 3
Chamber Tests

The chamber test protocol was developed to realistically model actual use conditions for the insect control article of the invention. A closed, generally featureless, approximately 28 m$^3$, box-like test chamber is used, the size of a small room. Six mosquito knock-down cages are distributed vertically within the test chamber, suspended from poles adjacent to opposite test chamber side walls, where they can be observed from outside the test chamber through chamber windows. Mosquitoes in the cages are observed during a test to evaluate the ability of a material being tested to knock down mosquitoes. An insect "knocked down" is one that is incapable of flying and usually is moribund in appearance. The insect may or may not actually be dead. The knockdown cages are cylindrical, approximately 6 cm long and 8 cm in diameter, and have screened but otherwise open ends.

Two repellency mosquito cages are also provided. The repellency cages are box-like screened cages, approximately 73 cm long and 16 cm square in cross section. All of the walls of the repellency cages are screened but otherwise generally open. Each repellency cage is divided by a clear plastic partition into a first holding area, which occupies approximately 45 cm of the length of the cage, and a second holding area, which occupies the remaining 28 cm. The plastic partition has a 4 cm diameter hole in its center that provides the only route by which mosquitoes may pass between the two holding areas. The repellency cages are mounted in a test chamber wall, with the plastic partition located in the plane of the test chamber wall, and are so oriented that the first holding area projects inwardly, into the test chamber, while the second holding area projects through the test chamber wall, out into normal room air.

A mouse cage essentially identical to a mosquito knockdown cage is mounted on the end of the first holding chamber of each repellency test cage that faces toward the interior of the test chamber. The mouse cage is separated from the repellency cage only by a mosquito-proof screen. One mouse is placed in the mouse cage during a test to provide an attractant for mosquitoes being held in the repellency test cage. Mosquitoes in the first holding area of a repellency cage thus are attracted toward the mouse, on the one hand, and repelled by the insect control article being tested, on the other hand.

When a test is run, fifty female mosquitoes are placed in the first holding area of each mosquito cage, with the partition hole closed by a removable door. Ten female mosquitoes are placed in each knock-down cage. The insect control article to be tested is placed centrally within the test chamber and the air flow is initiated. At timed intervals up to a total testing period of two hours, each knock-down cage and each repellency cage is visually examined, and the location, number, and condition of the mosquitoes are noted. The number of mosquitoes that have been driven to the second holding area provides a measure of the repellency of the insect control article being tested. The number of mosquitoes knocked down in the knock-down cages is also recorded. The general success of an insect control article is judged by both the mosquitoes repelled and those knocked down, in that both effects reduce the total number of mosquitoes available for biting.

Two series of tests were run using the chamber test protocol to evaluate the effect of insect control articles made in accordance with the invention. In the first series, pieces of cotton cloth approximately 645 cm$^2$ in size were impregnated with selected amounts of insect control active ingredients and were suspended several cm in front of a conventional, square, 51 cm (20 inch) household box fan, which provided the air flow required by the test protocol. The fan was located on the chamber floor, with its airflow directed toward one of the two, opposed ends of the test chamber in which no repellency cage was mounted. The times were recorded by which 50% (RD50) and 90% (RD90) of the mosquitoes had been repelled from the first holding area to the second, and by which 50% (KD50) of the mosquitoes had been knocked down. The results are summarized in the following table:

| Ingredient | Weight used in grams | Minutes to RD50 | Minutes to RD90 | Minutes to KD50 |
|---|---|---|---|---|
| Transfluthrin | 0.050 | 15 | 87 | 27 |
| Prallethrin | 0.0625 | 12 | 30 | 40 |
| Vaporthrin | 1.0 | 17.5 | 45 | 21 |
| DDVP | 1.0 | 17 | 25 | 21 |
| Esbiothrin | 0.5 | 23 | 111 | 55 |
| Citronella | 6.0 | 25 | NA | NA |
| Permethrin | 4.0 | 112 | NA | NA |
| Propoxur | 3.0 | 77 | NA | NA |
| Dursban | 4.0 | 96 | NA | NA |
| Cyfluthrin | 2.5 | NA | NA | NA |
| Allethrin | 0.05 | NA | NA | NA |
| Pyrethrum | 2.0 | NA | NA | NA |

[NA = not achieved]

These results demonstrate why the past teachings of the art with respect to passive evaporation of pyrethrum, pyrethroids and certain non-pyrethroid active insect control ingredients do not teach or even teach toward the present invention. Under this test, which closely models the situation of use of the invention, practical insect control as defined above was achieved only by transfluthrin, prallethrin, vaporthrin, esbiothrin, and DDVP. The superiority of vaporthrin to pyrethrum, for example, is quite unexpected in that pyrethrum actually performed twice as well as vaporthrin in the olfactometer tests. However, in the chamber test, even 2 grams of pyrethrum failed to achieve an RD50 within the two hour duration of the test, whereas half that amount of vaporthrin achieved an RD50 within 17.5 minutes. Among the non-pyrethroids, while DDVP was surprisingly successful, propoxur and Dursban were not, a distinction not predictable from the art. Furthermore, several of the insect control active ingredients that achieved an RD50, failed to achieve an RD90 within the two-hour testing period. While repelling half of the mosquitoes in a room shows undeniable activity, that performance level may still be too low to provide mosquito protection acceptable to a typical user.

Upon observation of the successful performance of transfluthrin and vaporthrin in the test just described, both ingredients were also tested for their ability to knock down *Musca domestica* (house flies), using the same protocol. Flies were held within knock-down cages identical to those used with mosquitoes, above. Repellency was not evaluated. The following results were observed:

| Ingredient | Weight used (in grams) | Minutes to KD50 | Minutes to KD90 |
|---|---|---|---|
| Transfluthrin | 0.125 g | 50 min | 102 min |
| Vaporthrin | 1.00 g | 49 min | 110 min |

These results demonstrate the effectiveness of the invention with respect to flying insects other than mosquitoes.

By way of comparison, a commercially available liquid evaporator device for insect control was tested by use of the chamber protocol just described, with the results set forth in the following table. Mosquitoes were the test insect. The device used was the liquid evaporator sold in Europe by S. C. Johnson & Son, Inc. of Racine, Wis. under the mark "45 Nights®." The device was charged with the liquid commercialy sold for use with that evaporator, which contains 6% pynamin forte as the insect control active ingredient.

| Minutes to RD50 | Minutes to RD90 | Minutes to KD50 |
|---|---|---|
| 45 | 60 | 30 |

These results demonstrate the reasonableness of the levels of control described above as the minimum and preferred practical insect control standards.

In an additional series of tests using the chamber protocol, two insect control active ingredients were tested for their ability to achieve the preferred practical control level, defined above. The experiment of the first series was substantially repeated except that the substrate was a 0.5 cm thick, 4.5 cm diameter coil of common corrugated cardboard, with the channels of the corrugation presented endwardly to the direction of air flow. Air flow was provided at the rate of approximately 0.06 m$^3$ (2 ft$^3$) per minute by a small blower device that directed air upwardly through an air passage of approximately the same diameter as the substrate and within which the substrate was held. The following results were achieved:

| Ingredient | Weight used in grams | Minutes to RD50 | Minutes to RD90 | Minutes to KD50 |
|---|---|---|---|---|
| Transfluthrin | 0.10 | 30 | 80 | 20 |
| Prallethrin | 0.918 | NA | NA | NA |

[NA = not achieved]

Again, the results of this second series were unexpected when compared to the results for transfluthrin and prallethrin in the first series. While time to RD50 was only 30 minutes for transfluthrin, for example, prallethrin failed to achieve an RD50 at any time during the two hour test. Because tefluthrin is nearly identical to transfluthrin chemically, comparable results would be expected for the two materials.

The effect was also measured of directly applying transfluthrin to the blades of the small blower used in the second series tests just described, to provide a direct comparison to the disclosure of Clarke. The chamber protocol described was utilized, and air flow was provided by the blower at the same rate of approximately 0.06 m$^3$ (2 ft$^3$) per minute. A total of 0.072 gm of transfluthrin was directly applied with a small artist's brush to the nine turbine blades of the small fan used in the blower tests. The was the insect control active ingredient that had proved itself successful in the previous chamber protocol test at that airflow rate. Nevertheless, RD50, RD90, and KD50 were never achieved within the two hour testing period, even though much more transfluthrin was being used than in the second series test just described. This test demonstrated the important advantage gained by locating the impregnated substrate at a selected location not in contact with any fan blades thereof.

Industrial Application

The control of flying insects generally and flies and mosquitoes in particular is of great practical interest. To their considerable annoyance and possible exposure to insect-borne disease, people and animals occupying unscreened buildings and shelters, as well as patios, picnic sites, and other interior and exterior locations, all are exposed to feeding mosquitoes, flies, and other biting or nuisance insects. A considerable industry provides repellent or insecticidal materials and devices to address the problem but not always with economical, long-lasting, efficacious results.

While the present invention has been described with respect to what is presently considered to be the preferred embodiments, it is to be understood that the invention is not limited to the disclosed embodiments. On the contrary, the invention is intended to cover various modifications and equivalent formulations included within the spirit and scope of the appended claims. The scope of the following claims is to be accorded the broadest interpretation so as to encompass all such modifications and equivalent formulations and functions.

What is claimed is:

1. A method for controlling flying insects comprising the steps of:

a. providing an insect control article having a substrate with an essentially open surface that is impregnated with an active insect control ingredient in a structure such that the ingredient will passively evaporate when exposed to air to control the flying insects, wherein the active insect control ingredient is selected from the group consisting of transfluthrin, prallethrin, tefluthrin, and combinations thereof, and wherein the insect control article includes attaching means for attaching the impregnated substrate to means for circulating air;

b. placing the insect control article in an environment with air movement by attaching the insect control article to means for circulating air at a selected location not in contact with any fan blades thereof and exposing the open surface of the insect control article to air circulated by the means for circulating air, wherein the environment is selected from the group consisting of outdoor areas, sleeping areas, and rooms of not less than 27 m$^3$; and c. allowing the active insect control ingredient impregnated within the substrate to passively evaporate into the air in an environment free of added haet;

d. wherein the substrate of the insect control article is selected from the group consisting of paper-board, open pore cellulosic materials, coiled corrugated paper, woven cloth and non-woven pads or felts of fiber, gels, and absorbent solid-porous foams.

2. The method for controlling flying insects of claim 1, wherein the active insect control ingredient of the insect control article is impregnated within the substrate in an amount of from 0.1 to 10 milligrams per square centimeter of the substrate macro surface area.

3. The method for controlling flying insects of claim 1, wherein the insect control article includes hanger means for hanging the impregnated substrate.

4. The method for controlling flying insects of claim 1, wherein the insect active control ingredient includes at least one of transfluthrin and tefluthrin.

5. The method for controlling flying insects of claim 1, wherein the insect active control ingredient includes transfluthrin.

* * * * *